United States Patent [19]
Slavtcheff et al.

[11] Patent Number: 5,814,313
[45] Date of Patent: Sep. 29, 1998

[54] THICKENED COSMETIC EMULSIONS

[75] Inventors: Craig Stephen Slavtcheff, Guilford, Conn.; Genaro Jaime Gonzalez, Jiutepec, Mexico; Machitje Jerrey Mokati, Durban, South Africa

[73] Assignee: Chesebrough-Pond's USA Co., Division of Conopco, Inc., Greenwich, Conn.

[21] Appl. No.: 715,661

[22] Filed: Sep. 18, 1996

[51] Int. Cl.$^6$ ............................................. A61K 31/74
[52] U.S. Cl. ........................ 424/78.03; 424/78.02; 424/78.08; 514/844; 514/873; 514/937; 252/315.1
[58] Field of Search .......................... 424/401, 403, 424/404, 408, 409, 419, 420, 449, 484, 485, 46, 47, 70.17, 70.22, 78.03, 78.08, 78.02; 549/430; 252/309, 78.5, 312, 351, 315.1, 315.2; 568/591, 608, 619; 510/101, 129, 152; 514/937, 873, 844

[56] References Cited

U.S. PATENT DOCUMENTS

| | | | |
|---|---|---|---|
| 4,428,860 | 1/1984 | Panek et al. | 252/315.1 |
| 4,491,526 | 1/1985 | Deck | 252/32.5 |
| 4,547,303 | 10/1985 | Deck et al. | 252/73 |
| 4,588,511 | 5/1986 | Frentrup et al. | 252/32.7 |
| 4,649,224 | 3/1987 | Panek et al. | 568/624 |
| 4,665,239 | 5/1987 | Panek et al. | 568/624 |
| 4,673,518 | 6/1987 | Owens et al. | 252/75 |
| 4,686,058 | 8/1987 | Schwartz et al. | 252/75 |
| 4,709,099 | 11/1987 | Panek et al. | 568/624 |
| 4,810,503 | 3/1989 | Carson et al. | 424/76.3 |
| 5,422,112 | 6/1995 | Williams | 424/401 |
| 5,539,129 | 7/1996 | Zysman et al. | 549/430 |
| 5,540,853 | 7/1996 | Trinh et al. | 510/101 |

*Primary Examiner*—Michael P. Woodward
*Assistant Examiner*—Datquan Lee
*Attorney, Agent, or Firm*—Milton L. Honig

[57] ABSTRACT

A cosmetic emulsion is provided which includes water, an oily emollient and a thickening/compatibilizing agent which is a polyether. The polyether is formed from the reaction of a copolymer of ethylene oxide with a $C_3$–$C_4$ alkylene oxide and a $C_{12}$–$C_{40}$ alpha-olefin epoxide or glycidyl ether.

3 Claims, No Drawings

THICKENED COSMETIC EMULSIONS

BACKGROUND OF THE INVENTION

1. Field of the Invention

The invention relates to the simultaneous thickening and compatibilizing of water and emollient oils into cosmetic emulsions.

2. The Related Art

Cosmetic compositions often require thickeners to achieve an aesthetically pleasing viscosity. Fluids that flow with a watery consistency too rapidly run off the treated skin areas. For a cosmetic to be effective, it often must have substantivity. Thickeners provide this substantivity. Furthermore, low viscosity formulas which may be skin effective, nevertheless through their wateriness signal ineffectiveness to the consumer. Products of watery consistency are also aesthetically displeasing to consumers with expectations of rich and creamy products.

Countless numbers of thickening agents are known in the literature. Perhaps this plethora intimates that not all thickening agents are equally effective for any particular type of formulation.

Water-based fluids intended for hydraulic or metalworking purposes can be thickened with ethoxylated polyethers. These are described in U.S. Pat. No. 4,491,526 (Deck) and U.S. Pat. No. 4,665,239 (Panek et al.). These references are concerned neither with cosmetic emollient oils nor water and oil emulsions.

U.S. Pat. No. 5,422,112 (Williams) illustrates a variety of thickeners for cosmetic compositions. These include combinations of a heterobiopolysaccharide gum (e.g. xanthan gum), an inorganic thickening agent (e.g. magnesium aluminum silicate) and a polyacrylamide. This system is particularly useful for building viscosity in relatively acidic compositions.

While known cosmetic thickeners improve viscosity, few if any function to compatibilize oil and water. Industry has long sought a material that could both thicken and compatibilize oily emollient with water to achieve stable emulsions. Most difficult is the achievement of a high volume (e.g. 10–90%) oil phase emulsion.

Accordingly it is an object of the present invention to provide a cosmetic product containing a thickening agent that can also compatibilize oil with water to achieve a stable emulsion.

It is another object of the present invention to provide a thickened water and oil cosmetic emulsion of sufficiently aesthetically consumer pleasing viscosity.

It is still another object of the present invention to provide a cosmetic product that is synergistically thickened as well as compatibilized.

Yet another object of the present invention is to provide a thickened emulsion which is quick breaking, light and has improved aesthetics.

These and other objects of the present invention will more readily become apparent from the summary, detailed description and examples which follow.

SUMMARY OF THE INVENTION

A cosmetic composition in emulsion form is provided which includes:

(i) from 1 to 90% by weight of water;
(ii) from 1 to 90% by weight of an oily cosmetic emollient; and
(iii) from 0.1 to 20% by weight of an alpha-olefin modified polyether.

DETAILED DESCRIPTION OF THE INVENTION

Now it has been discovered that alpha-olefin modified polyethers can compatibilize relatively high volumes of oily emollient with water into an emulsion. High volume oil phase emulsions are normally quite difficult to manufacture at low cost. Ordinarily quite expensive amounts of emulsifiers are necessary to achieve phase stability. The present invention has discovered that the use of very low levels of alpha-olefin polyethers will not only thicken such emulsions but can compatibilize the oil and water phases. It also has been found that the emulsion products have the added benefit of excellent consumer aesthetics.

Alpha-olefin modified polyethers of the present invention are characterized by average number molecular weights generally in the range 1,000 to 75,000, preferably from 1,000 to 40,000. Polyethers of this invention are formed from a mixture of ethylene oxide and at least one lower alkylene oxide having 3 to 4 carbon atoms reacted with at least one active hydrogen-containing compound initiator. The resultant substance is further reacted with at least one alpha-olefin oxide or glycidyl ether having a carbon chain length from 12 to 40 carbon atoms. The proportion of alpha-olefin oxide or glycidyl ether present in the polyether thickener may range from 1 to 20% by weight, based upon the total weight of the thickener. Polyethers of this invention are commercially available under the trademark Pluraflo® AT 301 from the BASF Corporation.

Amounts of the polyether present in the cosmetic emulsion will range from 0.1 to 20%, preferably from 1 to 10%, optimally from 2 to 5% by weight.

Water is a further important element of the present invention. Amounts of water may range from 1 to 90%, preferably from 40 to 80%, optimally from 50 to 75% by weight of the emulsion.

Compositions of this invention will be emulsions of the W/O or O/W variety. Most preferably they will have a high volume oil phase meaning that the oil phase will be at least 10%, preferably from 20 to 60% by weight.

A third element of the present invention is that of an oily emollient. This material may be selected from hydrocarbons, silicone oils, esters and combinations thereof. Amounts of these emollients may range from 1 to 90%, preferably from 10 to 50%, optimally from 15 to 40% by weight of the emulsion.

Hydrocarbon emollients of the present invention may be those selected from petroleum jelly, mineral oil, polyalpha-olefins having from $C_{20}$ to $C_{70}$ atoms, preferably from $C_{20}$ to $C_{50}$ (e.g. Ethylflo 162® which are polydecenes), and polyisobutylenes.

Silicone oil emollients of the present invention may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C., while cyclic materials typically have viscosities of less than about 10 centistokes.

Examples of preferred volatile, silicone oils useful herein include: Dow Corning 245 and Dow Corning 345

(manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company).

Esters are a further category of emollients. These esters may be selected from:

(1) Alkenyl esters of fatty acids having 10 to 20 carbon atoms. Examples thereof include oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearte, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterol esters, of which cholesterol fatty acid esters are examples thereof.

(6) Triglyceride esters such as vegetable and animal fats and oils. Examples include castor oil, cocoa butter, safflower oil, sunflower seed oil, cottonseed oil, corn oil, olive oil, cod liver oil, almond oil, avocado oil, palm oil, sesame oil, squalane and soybean oil.

(7) Acetoglyceride esters, such as actylated monoglycerides.

(8) Ethoxylated glycerides, such as ethoxylated glyceryl monostearate.

(9) Alkyl esters of fatty acids having 10 to 20 carbon atoms. Methyl, isopropyl and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diusopropyl adipate, diisohexyl adipate, dihexyldecyl adipate, diisopropyl sebacate, lauryl lactate, myristyl lactate, and cetyl lactate.

(10) Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

(11) Vegetable waxes including carnauba and candelilla waxes.

(12) Amides such as fatty acid amides, ethoxylated fatty acid amides, solid fatty acid alkanolamides.

Particularly useful are Guerbet esters (and Guerbet alcohols) as well as triglycerides such as sunflower seed oil.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include polyalkylene glycols and more preferably alkylene polyols and their derivatives, including propylene glycol, polyethylene glycol and derivatives thereof, sorbitol, hydroxypropyl sorbitol, hexylene glycol, 1,3-butylene glycol, 1,2,6-hexanetriol, glycerol, ethoxylated glycerol, propoxylated glycerol and mixtures thereof. For best results the humectant is preferably glycerol. The amount of humectant may range anywhere from 0.5 to 20%, preferably between 1 and 15% by weight of the composition.

Supplemental thickeners may be included in the compositions of this invention. Most especially it has been found that polyacrylamides can synergistically interact with the polyethers to provide an enhanced thickening of the system with good emulsion phase stability. The preferred polyacrylamide is available commercially under the trademark Sepigel 305® from Seppic, Inc., Fairfield, N.J. Small amounts of a $C_{13}$–$C_{14}$ Isoparaffin and Laureth-7 are present alongside the polyacrylamide in Sepigel 305®. Molecular weight of the polyacrylamide may range anywhere from 1000 up to 5 million. Preferably the polyacrylamide is a crosslinked polyacrylamide. Amounts of the polyacrylamide may range from 0.01 to 5%, preferably from 0.1 to 3%, optimally from 0.4 to 1% by weight. Relative weight amounts of the polyether to polyacrylamide may range from 10:1 to 1:5, preferably from 3:1 to 1:3, optimally from 1:1 to 1:2.

Compositions of the present invention may also include adjunct emulsifiers or surfactants which may be of the nonionic, anionic, cationic or amphoteric type. Examples of satisfactory nonionic emulsifiers include fatty alcohols having 10 to 20 carbon atoms condensed with 2 to 20 moles of ethylene oxide or propylene oxide, alkyl phenols with 6 to 12 carbon atoms condensed with 2 to 20 moles of ethylene oxide, mono and di-fatty acid esters of ethylene glycol wherein the fatty acid moiety contains from 10 to 20 carbon atoms, fatty acid monoglyceride wherein the fatty acid moiety contains from 10 to 20 carbon atoms and polyoxyethylene sorbitol or polyoxypropylene sorbitans. Amounts of the adjunct emulsifier may range from 0.1 to 20% by weight of the emulsion.

Among other additives which may be present in the compositions of this invention are fatty acids and alcohols having from 10 to 20 carbon atoms. Suitable examples of the fatty acids include pelargonic, lauric, myristic, palmitic, stearic, isostearic, hydroxystearic, oleic, linoleic, ricinoleic, arachidic, behenic, and erucic acids. Examples of fatty alcohols include lauryl, myristyl, cetyl, hexadecyl, stearyl, isostearyl, hydroxystearyl, oleyl, ricinoleyl, behenyl, erucyl, and 2-octyl dodecanyl alcohols. These materials may be present in amounts anywhere from 0.1 to 20% by weight of the composition.

Vitamin oils and essential oils may also be incorporated each at levels of 0.0001 to 5%.

Preservatives can desirably be incorporated into the cosmetic compositions of this invention to protect against the growth of potential harmful microorganisms. While it is in the aqueous phase that microorganisms tend to grow, microorganisms can also reside in the oil phase. As such, preservatives which have solubility in both water and oil are preferably employed in the present compositions. Suitable preservatives include alkyl esters of parahydroxybenzoic acid, hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methylparaben, imidazolidinyl urea, sodium dehydroxyacetate, propylparaben and benzyl alcohol. The preservative should be selected having regard for the use of the composition and possible incompatibilities between the preservative and other ingredients in the emulsion. Preservatives are preferably employed in amounts ranging from 0.01% to 2% by weight of the composition.

The following examples will more fully illustrate the embodiments of this invention. All parts, percentages and proportions referred to herein and in the appended claims are by weight unless otherwise indicated.

EXAMPLES 1–6

Emulsions illustrative of the present invention are outlined in Table I below.

TABLE I

| COMPONENT | EXAMPLE (WT. %) | | | | | |
|---|---|---|---|---|---|---|
| | 1 | 2 | 3 | 4 | 5 | 6 |
| PHASE A | | | | | | |
| Petroleum Jelly | 20 | 30 | 30 | 40 | 40 | 35 |
| Dow Corning 200 ® | 2.0 | 1.5 | 1 5 | 1.0 | 1.5 | 2.0 |
| Dow Corning 344 ® | 2.0 | 1.0 | 1.5 | 1.0 | 1.0 | 2.0 |
| Naturechem GMHS ® | 0.5 | 0.5 | 0.5 | 0.5 | 0.5 | .0.5 |
| PHASE B | | | | | | |
| PEG-6 | 3.0 | 5.0 | 2.0 | 3.0 | 3.0 | 3.0 |
| Puraflo AT ® 301 | 0.8 | 1.2 | 1.0 | 2.0 | 3.0 | 3.5 |
| Glydant Plus ® | 0.1 | 0.1 | 0.1 | 0.1 | 0.1 | 0.1 |
| Water | qs | qs | qs | qs | qs | qs |
| Sepigel 305 ® | 1.0 | 0.5 | 0.5 | 0.5 | — | — |

These examples are prepared by first combining Phase A components which are heated at 70° C. Phase B components are then combined in a main vessel. These are also heated with mixing at 70° C. Phase A is slowly added to Phase B with constant mixing. The combined phases are then slowly cooled to 45° C. Thereafter the Sepigel 305® is blended into the resultant product in those compositions where this material is present.

EXAMPLES 7–12

A further set of illustrative examples according to the present invention are provided in Table II below.

TABLE II

| COMPONENT | EXAMPLE (WT. %) | | | | | |
|---|---|---|---|---|---|---|
| | 7 | 8 | 9 | 10 | 11 | 12 |
| PHASE A | | | | | | |
| Petroleum Jelly | 20 | 30 | 30 | 40 | 40 | 35 |
| $C_{12}$—$C_{15}$ Alkyl Lactate | 10 | 15 | 5 | 8 | 8 | 6 |
| Cetiol 1414-E ® | 3.8 | 3.8 | 3.5 | 3.8 | 4.2 | 4 |
| Cetearyl Alcohol | 2.4 | 2.8 | 2.4 | 2.8 | 2.8 | 3 |
| Microwax | 2.0 | 2.0 | 10 | 1.0 | 1.0 | 1.0 |
| Vitamin E Acetate | 0.1 | 0.1 | 0.1 | 0.1 | 0.1 | 0.1 |
| PHASE B | | | | | | |
| Dry-Flo ® | 7.0 | 2.0 | 5.0 | 3.0 | 3.0 | 4.0 |
| Pluraflo AT ® 301 | 1.0 | 2.0 | 3.0 | 1.0 | 1.0 | 2.0 |
| Glycerin | 1.0 | 1.0 | 1.0 | 1.0 | 1.0 | 1.0 |
| Diglycerin | 1.0 | 1.0 | 1.0 | 1.0 | 1.0 | 1.0 |
| Glydant Plus ® | 0.1 | 2.0 | 3.0 | 1.0 | 1.0 | 2.0 |
| Water | qs | qs | qs | qs | qs | qs |

EXAMPLES 13–20

The following examples were prepared to evaluate a variety of oily emollients. Thus, examples 13–17 respectively focus upon petroleum jelly, mineral oil, sunflower seed oil, rice bran oil and a volatile hydrocarbon (Permethyl 101A®). Examples 18–20 were prepared to demonstrate changes in the level of Pluraflo AT® 301. Compositions prepared from all of the examples were placed in an oven at 60° C. to evaluate stability against phase separation. Stability was achieved in all compositions for at least five days, a period predictive of long term storage stability at temperatures normally encountered in consumer environments. All of the compositions produced thick creamy products.

TABLE III

| COMPONENT | EXAMPLE (WT. %) | | | | | | | |
|---|---|---|---|---|---|---|---|---|
| | 13 | 14 | 15 | 16 | 17 | 18 | 19 | 20 |
| PHASE A | | | | | | | | |
| Petroleum Jelly | 30 | — | — | — | — | 30 | 30 | 30 |
| Mineral Oil | — | 30 | — | — | — | — | — | — |
| Sunflower Seed Oil | — | — | 30 | — | — | — | — | — |
| Rice Bran Oil | — | — | — | 30 | — | — | — | — |
| Permethyl 101A ® | — | — | — | — | 20 | — | — | — |
| Dow Corning 200 ® | 0.75. | 0.75 | 0.75 | 0.75 | 0.75 | 0.75 | 0.75 | 0.75 |
| Dow Corning 245 ® | 0.5 | 0.5 | 0.5 | 0.5 | 0.5 | 0.5 | 0.5 | 0.5 |
| PHASE B | | | | | | | | |
| Glycerin | 5.0 | 5.0 | 5.0 | 5.0 | 5.0 | 5.0 | 5.0 | 5.0 |
| PEG-6 | 1.0 | 1.0 | 1.0 | 1.0 | 1.0 | 1.0 | 1.0 | 1.0 |
| Pluraflo AT ® 301 | 1.0 | 1.0 | 1.0 | 1.0 | 1.0 | 1.0 | 1.0 | 1.0 |
| Glydant Plus ® | 0.1 | 0.1 | 0.1 | 0.1 | 0.1 | 0.1 | 0.1 | 0.1 |
| Disodium EDTA | 0.05 | 0.05 | 0.05 | 0.05 | 0.05 | 0.05 | 0.05 | 0.05 |
| Water | qs | qs | qs | qs | qs | qs | qs | qs |

TABLE IV

Physical Properties

| PROPERTY | EXAMPLE | | | | | | | |
|---|---|---|---|---|---|---|---|---|
| | 13 | 14 | 15 | 16 | 17 | 18 | 19 | 20 |
| pH | 6.5 | 6.5 | 6.5 | 6.7 | 6.5 | 6.5 | 6.5 | 6.8 |
| Viscosity × $10^3$ (cps) | 85 | 75 | 68 | 87 | 54 | 104 | 81 | 121 |
| Stability at 60° C. (days) | 5 | 6 | 7 | 8 | 7 | 9 | 8 | 8 |

EXAMPLE 22–29

These examples were prepared to evaluate the effect of different concentrations of polyether and polyacrylamide.

TABLE V

| COMPONENT | EXAMPLE (WT. %) | | | | | | | |
|---|---|---|---|---|---|---|---|---|
| | 22 | 23 | 24 | 25 | 26 | 27 | 28 | 29 |
| PHASE A | | | | | | | | |
| Sunflower Seed Oil | 2.0 | 2.0 | 2.0 | 2.0 | 2.0 | 2.0 | 2.0 | 2.0 |
| Rice Bran Oil | 2.0 | 2.0 | 2.0 | 2.0 | 2.0 | 2.0 | 2.0 | 2.0 |
| Isononyl Isononoate | 2.0 | 2.0 | 2.0 | 2.0 | 2.0 | 2.0 | 2.0 | 2.0 |
| Tween 20 ® | 1.0 | 1.0 | 1.0 | 1.0 | 1.0 | 1.0 | 1.0 | 1.0 |
| Dow Corning 200 ® | 0.75 | 0.75 | 0.75 | 0.75 | 0.75 | 0.75 | 0.75 | 0.75 |
| Dow Corning 245 ® | 0.5 | 0.5 | 0.5 | 0.5 | 0.5 | 0.5 | 0.5 | 0.5 |
| PHASE B | | | | | | | | |
| Glycerin | 5.0 | 5.0 | 5.0 | 5.0 | 5.0 | 5.0 | 5.0 | 5.0 |
| PEG-6 | 1.0 | 1.0 | 1.0 | 1.0 | 1.0 | 1.0 | 1.0 | 1.0 |
| Pluraflo AT ® 301 | 1.0 | 2.0 | 0.5 | 0.5 | — | 0.5 | 0.25 | 2.0 |
| Sepigel 305 ® | 0.5 | 0.5 | 1.0 | 2.0 | 1.0 | 2.0 | 2.0 | 0.25 |
| Glydant Plus ® | 0.1 | 0.1 | 0.1 | 0.1 | 0.1 | 0.1 | 0.1 | 0.1 |
| Disodium EDTA | 0.05 | 0.05 | 0.05 | 0.05 | 0.05 | 0.05 | 0.05 | 0.05 |
| Water | qs | qs | qs | qs | qs | qs | qs | qs |

TABLE VI

Physical Properties

| PROPERTY | EXAMPLE | | | | | | | |
|---|---|---|---|---|---|---|---|---|
| | 22 | 23 | 24 | 25 | 26 | 27 | 28 | 29 |
| pH | 6.1 | 6.1 | 6.2 | 6.1 | 6.1 | 6.12 | 6.21 | 6.43 |
| Viscosity × $10^3$ (cps) | 25 | 32 | 32 | 45 | 4 | 21 | 18 | 17.5 |
| Stability at 60° C. (days) | 10 | 8 | 9 | 9 | very thin | 11 | 8 | 11 |

The foregoing description and examples illustrate selected embodiments of the present invention. In light thereof, various modifications will be suggested to one skilled in the art all of which are within the spirit and purview of this invention.

What is claimed is:

1. A cosmetic emulsion composition comprising:

(i) from 1 to 90% by weight of water;

(ii) from 1 to 90% by weight of an oily cosmetic emollient selected from the grout of hydrocarbons, silicone oils, esters and combinations thereof, the esters being selected from the group consisting of triglycerides, Guerbet esters and combinations thereof;

(iii) from 0.1 to 20% by weight of an alpha-olefin modified polyether formed from the reaction of a copolymer of ethylene oxide and at least one lower $C_3$–$C_4$ alkylene oxide with a $C_{12}$–$C_{40}$ alpha-olefin oxide or glycidyl ether; and (iv) from 0.1 to 5% by weight of polyacrylamide.

2. The composition according to claim 1 further comprising from 0.0001 to 5% each of vitamin and essential oils.

3. The composition according to claim 1 wherein the emollient is petroleum jelly.

\* \* \* \* \*